(12) United States Patent
Shine

(10) Patent No.: US 8,273,385 B1
(45) Date of Patent: Sep. 25, 2012

(54) ORAL RINSE COMPOSITION AND METHOD

(75) Inventor: Lawrence J. Shine, Kansas City, MO (US)

(73) Assignee: Thres Flo, LLC, Kansas City, MO (US)

( * ) Notice: Subject to any disclaimer, the term of this patent is extended or adjusted under 35 U.S.C. 154(b) by 206 days.

(21) Appl. No.: 12/626,102

(22) Filed: Nov. 25, 2009

Related U.S. Application Data

(63) Continuation of application No. 12/253,797, filed on Oct. 17, 2008, now abandoned.

(51) Int. Cl.
*A61K 8/22* (2006.01)
(52) U.S. Cl. ........ 424/725; 424/726; 424/736; 424/737; 424/747; 424/766; 424/53; 424/58
(58) Field of Classification Search .................... 424/50, 424/405
See application file for complete search history.

(56) References Cited

U.S. PATENT DOCUMENTS

| | | | |
|---|---|---|---|
| 4,923,685 A | 5/1990 | Wuelknitz et al. | |
| 4,945,087 A | 7/1990 | Talwar et al. | |
| 5,082,653 A | 1/1992 | Pan et al. | |
| 5,891,422 A | 4/1999 | Pan et al. | |
| 5,906,811 A | 5/1999 | Hersh | |
| 5,908,613 A | 6/1999 | Bozzacco | |
| 6,348,187 B1 | 2/2002 | Pan et al. | |
| 6,350,435 B1 | 2/2002 | Alvarez Hernandez | |
| 6,511,683 B1 | 1/2003 | Gahler | |
| 6,555,093 B2 | 4/2003 | Alvarez Hernandez | |
| 6,589,513 B2 | 7/2003 | Lesky et al. | |
| 6,706,256 B2 | 3/2004 | Lawlor | |
| 6,743,449 B2 | 6/2004 | Pinnell et al. | |
| 7,258,876 B2 | 8/2007 | Bozzacco | |
| 2002/0146666 A1 | 10/2002 | Sagel et al. | |
| 2003/0007937 A1 | 1/2003 | Lawlor | |
| 2006/0051384 A1* | 3/2006 | Scholz et al. | 424/405 |
| 2006/0251590 A1 | 11/2006 | Redmond et al. | |
| 2007/0053849 A1* | 3/2007 | Doyle et al. | 424/50 |

OTHER PUBLICATIONS

Office Action in U.S. Appl. No. 12/253,797 dated Apr. 2, 2009.
Office Action in U.S. Appl. No. 12/253,797 dated Jul. 1, 2009.
Office Action in U.S. Appl. No. 12/253,797 dated Oct. 9, 2009.

* cited by examiner

*Primary Examiner* — Walter Webb
(74) *Attorney, Agent, or Firm* — Hovey Williams LLP

(57) ABSTRACT

New oral rinse solutions and mouthwashes are provided. The oral rinse solutions comprise essential oil and alcohol, supplemented with hydrogen peroxide, and natural extracts. The essential oil and/or alcohol can be provided as part of a base composition. The most preferred base compositions are antiseptic mouthwashes containing the essential oil and/or alcohol. Alternatively, the ingredients can be individually added to the inventive composition. The oral rinse solutions provide antimicrobial activity while soothing oral inflammations and irritations, thus being useful for treating, alleviating, and promoting healing of a wide variety of oral ailments such as periodontal disease (gingivitis and periodontitis), plaque, oral inflammation, toothaches, oral ulcerations, dry socket, dentin hypersensitivity, and halitosis, as well as address aesthetic issues such as bad breath and tooth discoloration.

9 Claims, No Drawings

ORAL RINSE COMPOSITION AND METHOD

CROSS-REFERENCE TO RELATED APPLICATIONS

The present application is a continuation of co-pending U.S. patent application Ser. No. 12/253,797, entitled ORAL RINSE COMPOSITION AND METHOD, and filed Oct. 17, 2008, the benefit of which is claimed, and which is incorporated by reference herein in its entirety.

BACKGROUND OF THE INVENTION

1. Field of the Invention

The present invention is broadly concerned with improved oral rinses and mouthwashes and methods of making and using the same.

2. Description of the Prior Art

A variety of mouthwashes and oral rinses have been developed for treatment of conditions such as periodontal disease (gingivitis and periodontitis), plaque, oral inflammation, toothaches, oral ulcerations, dry socket, dentin hypersensitivity, and halitosis, as well as to address aesthetic issues such as bad breath and tooth discoloration.

For example, patients with advanced periodontal disease are often prescribed a germicidal mouthwash containing Chlorhexidine gluconate, commercially available under the brand names such as PERIDEX® (Procter & Gamble Co.; Cincinnati, Ohio) and PERIOGARD® (Colgate-Palmolive Co.; New York, N.Y.). However, one known side-effect of chorhexidine gluconate is that it can stain teeth and dental work. It is also reported as having a terrible taste, leaving an unpleasant aftertaste in the mouth, and even altering the patient's overall taste perception.

LISTERINE®-brand mouthwash (Warner-Lambert Co.; Morris Plains, N.J.) is another well-known mouthwash with antiseptic properties used to treat gingivitis and bad breath. These mouthwashes generally have a high alcohol (ethanol) content of between 21.6% and 26.9% by volume (v/v) based upon the total mouthwash volume. Eucalyptol, thymol, menthol, and methyl salicylate are listed as the active ingredients in LISTERINE®. Many patients who are suffering from painful irritations and inflammations in the oral cavity cannot tolerate the burning and/or stinging sensations associated with LISTERINE® and other similarly-formulated antiseptic mouthwashes.

Patients who are prescribed or recommended to use these mouthwashes such as LISTERINE® and PERIDEX® often fail to follow-through with actually using the mouthwash as prescribed because of the disagreeable side-effects of these mouthwashes. As a consequence, their overall oral health can be adversely affected. Thus, there is a need for an oral rinse that soothes and relieves oral inflammations while preventing and reducing the germs that cause periodontal disease and bad breath, without the adverse taste, burning sensations, or other side effects experienced with existing mouthwashes.

SUMMARY OF THE INVENTION

The present invention overcomes these problems by broadly providing novel oral rinse compositions having antimicrobial properties that also alleviate and soothe oral irritations.

More particularly, the present invention provides an oral rinse composition. The composition comprises an essential oil, hydrogen peroxide, less than about 20% v/v alcohol, and a natural extract. The essential oil is preferably selected from the group consisting of eucalyptol, menthol, methyl salicylate, thymol, tea tree oil, peppermint, spearmint, clove, and mixtures thereof. The natural extract is preferably selected from the group consisting of antioxidants, immune stimulants, and mixtures thereof.

The present invention is also directed toward a method of treating an oral area afflicted with an ailment. The method comprises contacting the oral area with the inventive composition, and retaining the composition in contact with the oral area for at least 30 seconds.

In another embodiment, the present invention provides a further oral rinse composition. The composition comprises hydrogen peroxide, less than about 20% v/v alcohol, from about 0.001% to about 0.10% w/v grape seed extract, from about 0.005% to about 1.0% v/v citrus seed extract, from about 0.005% to about 1.0% v/v immune stimulant, from about 0.001% to about 0.065% v/v tea tree oil, from about 0.005% to about 0.50% v/v of a first essential oil selected from the group consisting of peppermint oil, spearmint oil, clove oil, and mixtures of the foregoing, and a second essential oil selected from the group consisting of eucalyptol, menthol, methyl salicylate, and thymol.

In a yet another aspect, a method of preparing an oral rinse composition is provided. The method comprises dissolving a quantity of grape seed extract in water to form an aqueous solution; mixing a quantity of immune stimulant with the aqueous solution; dispersing a quantity of citrus seed extract in a first container comprising alcohol; dispersing a quantity of essential oils in a second container comprising alcohol; combining the first container of alcohol with the second container of alcohol to yield a combined alcohol solution; mixing the aqueous solution with the combined alcohol solution to yield an aqueous alcohol mixture; and mixing a quantity of hydrogen peroxide with the aqueous alcohol mixture to yield the oral rinse composition.

Advantageously, the inventive compositions promote oral health without the adverse side effects experienced with existing mouthwashes. Other advantages of the present invention will become apparent based upon the detailed description below, which illustrates preferred embodiments of the present invention.

DETAILED DESCRIPTION OF THE PREFERRED EMBODIMENTS

In more detail, the inventive oral rinse compositions comprise an essential oil, hydrogen peroxide, alcohol, and a natural extract. Suitable essential oils are selected from the group consisting of eucalyptol, menthol, methyl salicylate, thymol, tea tree oil, peppermint, spearmint, clove and mixtures thereof. The inventive compositions preferably comprise from about 0.01% to about 0.50% total essential oils, more preferably from about 0.05% to about 0.35%, even more preferably from about 0.10% to about 0.25%, with about 0.21% to about 0.23% being the most preferred, based upon the total volume of the oral rinse composition taken as 100% by volume. The essential oils used in the inventive oral rinse compositions provide antimicrobial activity, as well as act as flavoring agents and natural analgaesics. According to one aspect of the invention, tea tree oil is included in the composition to enhance the antiseptic properties of the oral rinse.

Eucalyptol, menthol, methyl salicylate, and/or thymol can be individually added to the composition, or they can be added via a base composition. Such base compositions include antiseptic mouthwashes containing these oils, such as LISTERINE®-brand mouthwash and similarly formulated generic brands. Thus, if preferred, the inventive oral rinses comprise an antiseptic mouthwash, hydrogen peroxide, and a natural extract. Additional antiseptic mouthwashes that could be used in the present invention are those that contain an effective amount of an antimicrobial agent or similar active ingredient selected from the group consisting of hexetidine, benzalkonium chloride, quaternary morpholinium alkyl, sulfates, cetylpyridinium chloride, cetylpyridinium bromide alkyldimethyl benzylammonium chloride, alkyltrimethyl ammonium halides, methylparaben, domiphen bromide, and mixtures thereof. Such base compositions can include alcohol or can be alcohol-free. However, those containing active essential oils dispersed in alcohol, such as LISTERINE®-type mouthwashes are particularly preferred. The preparation of suitable base compositions is described in U.S. Pat. No. 5,891,497 and U.S. Pat. No. 4,945,087, incorporated by reference herein.

Alternatively, the essential oils present can be added to the inventive composition individually. Eucalyptol is preferably included in the composition in an amount of from about 0.001% to about 0.10% w/v, more preferably from about 0.01% to about 0.07% w/v, even more preferably from about 0.025% to about 0.035% w/v, and most preferably from about 0.028% to about 0.03% w/v. As used herein, the percentage "weight by volume" of the ingredient in the solution (hereinafter referred to as "% w/v") is calculated based upon the total mass of the ingredient in grams per 100 ml of the final solution. Menthol is preferably included in the composition in an amount of from about 0.0005% to about 0.05% w/v, more preferably from about 0.005% to about 0.035% w/v, even more preferably from about 0.010% to about 0.0175% w/v, and most preferably from about 0.012% to about 0.016% w/v. Methyl salicylate is preferably included in the composition in an amount of from about 0.0007% to about 0.075% w/v, more preferably from about 0.006% to about 0.05% w/v, even more preferably from about 0.015% to about 0.025% w/v, and most preferably from about 0.018% to about 0.022% w/v. Thymol is preferably present in the composition in an amount of from about 0.0008% to about 0.08% w/v, more preferably from about 0.0065% to about 0.0575% w/v, even more preferably from about 0.016% to about 0.027% w/v, and most preferably from about 0.019% to about 0.023% w/v.

As noted above, the composition can also include peppermint and/or spearmint oil and/or clove oil. These oils can be provided alone or in combination. Regardless, the total amount of peppermint, spearmint, and/or clove oil in the final oral rinse composition should be from about 0.005% to about 0.50% v/v, preferably from about 0.015% to about 0.35% v/v, more preferably from about 0.025% to about 0.25% v/v, and most preferably from about 0.031% to about 0.15% v/v. As used herein, the percentage "by volume" of the ingredient in the composition (hereinafter referred to as "% v/v") is calculated based upon the volume of the total volume of the ingredient in ml per 100 ml of the final solution.

Tea tree oil contains a number of beneficial compounds such as terpinen-4-ol, which contributes to antimicrobial activity of the oil, as well as various other terpenes. It also exhibits antioxidant activity. Thus, when present in the inventive oral rinse solutions, tea tree oil is preferably included in the composition in an amount of from about 0.001% to about 0.065% v/v, more preferably from about 0.015% to about 0.045% v/v, even more preferably from about 0.025 to about 0.040%, and most preferably from about 0.031% to about 0.035% v/v.

Hydrogen peroxide acts as a debriding agent, and may also contribute to removing stains from tooth enamel with regular use of the inventive oral rinse. Preferably, hydrogen peroxide is included in the composition as a 3% solution, available as an over-the-counter peroxide solution. Hydrogen peroxide should be included in the composition in an amount of from about 15% to about 65% v/v, more preferably from about 20% to about 45% v/v, even more preferably from about 25% to about 40% v/v, and most preferably from about 30% to about 35% v/v.

Alcohols suitable for use in the inventive oral rinse compositions are preferably $C_1$-$C_5$ alcohols, more preferably the alcohol is selected from the group consisting of ethanol, 1-propanol, 2-propanol, 1-butanol, 2-butanol, 2-methyl-2-propanol, propylene glycol, and mixtures thereof. Ethanol, 1-propanol, and 2-propanol are preferred, as is a combined mixture of ethanol and 1-propanol. The inventive compositions preferably comprise less than about 20% by volume alcohol. Preferably, alcohol is included in the composition in an amount of from about 3.0% to about 15% v/v, more preferably from about 5% to about 10.0% v/v, even more preferably from about 6.5% to about 9.5% v/v, and most preferably from about 7% to about 9.0% v/v. According to a particularly preferred embodiment, the inventive compositions comprise less than about 7.5% by volume alcohol. When present, the alcohol acts as a solvent or carrier for the water-insoluble ingredients and can be added individually, or it can be added as part of a base composition including alcohol.

Alternatively, the inventive compositions can be essentially alcohol-free. That is, such compositions comprise less than about 1.0% by volume alcohol, preferably less than about 0.5% v/v alcohol, more preferably less than about 0.1% v/v alcohol, and even more preferably about 0% v/v.

Suitable natural extracts for use in the inventive oral rinse compositions include those selected from the group consisting of antioxidants, immune stimulants, and combinations of the foregoing. Such extracts contain a wide variety of phytochemicals such as polyphenols, flavanols, proanthocyanains, and other phytochemicals thought to contribute to healing of inflammation in the oral cavity, promote healthy gum tissue, as well as inhibit the growth of bacteria.

Preferred antioxidants are selected from the group consisting of grape seed extract, citrus seed extract, olive leaf extract, and mixtures thereof. Suitable citrus seed extracts include those selected from the group consisting of grapefruit seed extract, bitter orange extract, orange extract, lemon extract, lime extract, and mixtures thereof, with grapefruit seed extract being particular preferred. Grape seed extract can be included in the inventive compositions in an amount of from about 0.001% to about 0.10% w/v, preferably from about 0.010% to about 0.060% w/v, more preferably from about 0.025% to about 0.055% w/v, and most preferably from about 0.032% to about 0.041% w/v. Citrus seed extract can be included in the composition in an amount of from about 0.005% to about 1.0% v/v, preferably from about 0.05% to about 0.50% v/v, more preferably from about 0.10% to about 0.30% v/v, and most preferably from about 0.15% to about 0.21% v/v. The grape seed extract is preferably provided in a powder form, while the citrus seed extract is preferably provided as a liquid.

According to a further embodiment, the inventive oral rinse compositions will comprise olive leaf extract. Olive leaf extract contains antioxidants such as oleuropein and hydroxytyrosol, as well as triterpenoids, sterols, flavonoids, and various other phenolic acids. Olive leave extract can be present in the inventive oral rinse composition in an amount of from about 0.01% to about 2.0% v/v, preferably from about 0.10% to about 1.0% v/v, more preferably from about 0.25% to about 0.75% v/v, and most preferably from about 0.40% to about 0.60% v/v. Additional antioxidants that can be included in the composition include those selected from the group consisting of co-enzyme Q-10, pine bark extract, vitamin A, vitamin C, vitamin E, zinc, and combinations of the foregoing.

Preferred immune stimulants for use in the inventive compositions are selected froth the group consisting Echinacea (flower and root), Goldenseal, Hawthorne Berry, Myrrh, Rosehips, Lomatium dissectum, Astragalus root, Licorice root, and mixtures thereof, with Echinacea extract being particularly preferred. Immune stimulants can be included in the composition in an amount of from about 0.005% to about 1.0% v/v, preferably 0.05% to about 0.50% v/v, more preferably from about 0.10% to about 0.30% v/v, and even more preferably from about 0.15% to about 0.21% v/v. Immune stimulants can be added to the composition individually or as part of a base composition containing one or more immune stimulants. A particularly preferred source of immune stimulants is described in U.S. Pat. No. 6,511,683, and commercially available under the name ECHINAMIDE® Anti-V Formula (Natural Factors; Coquitlam, British Columbia, Canada). Other preferred sources include Nature's Apothecary Echinacea Flowering Tops and Roots (*Echinacea purpurea* and *E. angustifolia*) (Bloomingdale, Ill.), Organic Insure Immune Support Liquid by Zand® (Ferndale, Wash.), and Teeter Creek's Echinacea & Goldenseal Root Tincture (Ava, Mo.).

The inventive compositions may also include baking soda to clean teeth and tone gums. When used in conjunction with the hydrogen peroxide, the baking soda can also help remove tooth discoloration and control tartar buildup. When included in the composition, the baking soda is preferably present in an amount of from about 0.05% to about 1.0% w/v, preferably from about 0.16% to about 0.50% w/v, and even more preferably from about 0.24% to about 0.48% w/v. In a further aspect, the compositions can include salt (sodium chloride, potassium chloride, etc.) to help disinfect oral lesions. Salt may also contribute to the removal of stains and cleaning gums. When included in the composition, the level of salt can be from about 0.06% to about 0.50% w/v, preferably from about 0.10% to about 0.30% w/v, and even more preferably from about 0.12% to about 0.25% w/v.

To enhance the flavor of the inventive oral rinse without contributing to tooth decay and bacterial growth, sugar alcohols can be included in the inventive compositions. Suitable sugar alcohols include those selected from the group consisting of xylitol, sorbitol, mannitol, maltitol, lactitol, isomalt, hydrogenated starch hydrosylate, erthyritol, and mixtures thereof. The most preferable sugar alcohol is sorbitol, and it can be included in the composition in an amount of from about 0.50% to about 20% v/v, preferably from about 1.0% to about 18% v/v, more preferably from about 3.0% to about 15% v/v, and even more preferably from about 5.0% to about 11% v/v. The sugar alcohol can be individually added to the composition, or it can be added via a base composition including one or more sugar alcohols. It will be appreciated that the concentration of sugar alcohol in the oral rinse composition can be varied depending on the desired flavor and taste of the final solution and the sweetness level of the sugar alcohol (and other sweeteners) used.

To aid in the complete dispersion of the ingredients in the oral rinse solution and throughout the oral area during use, nonionic surfactants can be included in the composition. Suitable non-ionic surfactants are selected from the group consisting of poly(oxyethylene)-poly(oxypropylene) block copolymers, condensates of ethylene oxide with polymers of propylene oxide, and amphoteric agents such as quarternized imidazole derivatives, with poly(oxyethylene)-poly(oxypropylene) block copolymers being the most preferred. These block copolymers are commercially known as poloxamers. Preferred poloxamers are those that are non-toxic and approved as direct food additives by the Food and Drug Administration. A preferred poloxamer is poloxamer 407, which is commercially available under the name PLURONIC®F-127 (available from BASF Corp.; Florham, N.J.). The non-ionic surfactant is preferably included in the composition in an amount of from about 0.008% to about 0.30% v/v, more preferably from about 0.01% to about 0.25% v/v, even more preferably from about 0.02% to about 0.20% v/v, and most preferably from about 0.03% to about 0.18% v/v. The level of surfactant can be modified depending upon the properties of the alcohol solvent used and the level of other ingredients in the final oral rinse solution. The non-ionic surfactant can be individually added to the composition, or it can be added via a base composition including the surfactant.

It will be appreciated that the inventive compositions can also include additional optional ingredients without going beyond the scope of the invention, such as those selected from the group consisting of natural and artificial flavorings and artificial sweeteners, preservatives, buffer systems, humectants, and coloring, depending upon individual tastes. Examples of natural flavoring agents can include anethole, anise oil, camphor, cinnamon oil, eugenol, lavender oil, phenyl salicylate, methol, pine oil, lemon, lime, orange, wintergreen oil, and thyme oil. Examples of artificial sweeteners include saccharin (sodium saccharin), aspartame, sucralose, neotame, and acesulfame potassium. Preservatives and buffer systems include those selected from the group consisting of sodium benzoate/benzoic acid, sodium citrate/citric acid, and any other weak acids or weak bases and their corresponding salts that are approved as direct food additives by the FDA. These ingredients can be added individually or in a group as part of another composition, such as a base composition containing these ingredients. Depending upon the desired final product, the aqueous mixture may also include thickening and gelling agents to provide the compositions with a particular consistency. For example, petrolatum could be included in a formulation intended for topical application of the composition.

It is preferred that the pH in the final oral rinse composition is at a level of from about 4.0 to about 6.5, and more preferably from about 4.5 to about 6.0.

Broadly, the inventive composition is formed by dissolving or dispersing in a quantity of distilled water the grape seed extract, tea tree oil (if present), and immune stimulant. Preferably, the grape seed extract is first dissolved in a quantity of distilled water by heating the solution to a temperature of from about 35° C. to about 60° C., preferably from about 40° C. to about 55° C., and more preferably from about 43° C. to about 50° C. This solution is then stirred and preferably filtered prior to adding the immune stimulant. When present in the composition, tea tree oil is preferably mixed into the heated grape seed extract and water solution after filtering. Even more preferably, the resulting solution is filtered again prior to adding the immune stimulant. The water insoluble ingredients (e.g., essential oils, etc.) are then dispersed in a quantity of alcohol at ambient temperatures along with the citrus seed extract. The water and alcohol solutions are then mixed at ambient temperature. Preferably, the water solution is mixed into the alcohol solution. The hydrogen peroxide and olive leaf extract (if present) is then mixed with the water/alcohol solution. Preferably, the hydrogen peroxide is mixed into the water/alcohol solution, followed by the olive leaf exact (when present). Finally, the pH of the solution is adjusted using a buffer system. Preferably, the buffer system is selected from the group consisting of sodium benzoate/ benzoic acid, sodium citrate/citric acid, and any other weak acids or weak bases and their corresponding salts that are approved as direct food additives by the FDA.

EXAMPLES

The following examples set forth preferred methods in accordance with the invention. It is to be understood, however, that these examples are provided by way of illustration and nothing therein should be taken as a limitation upon the overall scope of the invention.

Example 1

Preparation of Oral Rinse Compositions

In this example, various oral rinse compositions were prepared from the ingredients in the tables below.

TABLE 1

Formulation A

| Ingredient | Quantity |
| --- | --- |
| Antiseptic Mouthwash[A] | 1000 ml |
| Distilled water | 1000 ml |
| Hydrogen peroxide (3% solution) | 946.35 ml |
| Grape Seed Extract powder | 1000 ml |
| Immune Stimulant Extract[B] | 5 ml |
| Grapefruit Seed Extract | 5 ml |
| Essential Oil(s)[C] | 1 ml |

[A]Generic version of LISTERINE ® antiseptic mouthwash (Active Ingredients: Eucalyptol (0.092%), Menthol (0.042%), Methyl Salicylate (0.060%), Thymol (0.064%); Inactive Ingredients: Alcohol (21.6%), Water, Sorbitol solution, Flavoring, Poloxamer 407, Benzoic acid, sodium saccharin, sodium benzoate, FDC green No. 3).
[B]ECHINAMIDE ® Anti-V Formula, Natural Factors; Coquitlam, British Columbia, Canada.
[C]Peppermint oil, spearmint oil, clove oil, and combinations of the foregoing.

The detailed procedure for preparing Formulation A is as follows. It was found that the order of mixing the ingredients is critical to decreasing the turbidity and cloudiness of the final solution.

First, three separate solutions were made. For the first solution, the grape seed extract powder (GNC Herbal Plus® Standardized Grape Seed Extract; Pittsburgh, Pa.) was stirred into 1000 ml of distilled water. The solution was heated for 1-2 minutes in the microwave at low power until it reached a temperature of about 43-45° C. The solution was then filtered through filter paper (40 cm, Scientific Specialities; Holly Springs, Pa.). Next, the immune stimulant extract was added to the filtered heated solution and stirred. In a separate container, 100 ml of the antiseptic mouthwash were measured out, reserving the rest, and the grapefruit seed extract (Nutribiotic GSE Liquid Concentrate; Lakeport, Calif.) was added and mixed well to form the second solution. The remaining antiseptic mouthwash (900 ml) was placed in a third container. Next, 1 ml of peppermint oil (NOW® Personal Care, Certified Organic; Bloomingdale, Ill.) was added to the mouthwash, stirring vigorously until well-mixed, forming the third solution.

The second and third solutions were then combined. Specifically, the 100 ml mouthwash/grapefruit seed extract solution was added to the container containing the 900 ml of mouthwash/essential oils solution. The combined solution was then placed in a large container. The first solution (aqueous solution) was then added to the combined mouthwash solution and stirred for about 30 seconds. Finally, the 3% solution of hydrogen peroxide was added and the entire solution was lightly stirred to yield the inventive oral rinse solution.

The above procedure was repeated, except that the 1 ml of peppermint oil was replaced by a combination of 0.5 ml of peppermint oil and 0.5 ml of spearmint oil to yield a further composition. The above procedure was again repeated, except that the 1 ml of peppermint oil was replaced by 1 ml of clove oil yielding a third composition.

The pH of the resulting oral rinse composition was about 5.5-6.0.

TABLE 2

Formulation B

| Ingredient | Quantity |
| --- | --- |
| Antiseptic Mouthwash[A] | 1000 ml |
| Distilled water | 1000 ml |
| Hydrogen peroxide (3% solution) | 946.35 ml |
| Grape Seed Extract powder | 1200 mg |
| Immune Stimulant Extract[B] | 6 ml |
| Grapefruit Seed Extract | 6 ml |
| Tea Tree Oil | 1 ml |
| Essential Oil(s)[C] | 3 ml |

[A]Same mouthwash from Formulation A.
[B]ECHINAMIDE ® Anti-V Formula, Natural Factors; Coquitlam, British Columbia, Canada.
[C]Peppermint oil, spearmint oil, clove oil, and combinations of the foregoing.

The detailed procedure for preparing Formulation B is as follows. As outlined for Formulation A above, three separate solutions were made. For the first solution, the grape seed extract powder was stirred into 1000 ml of distilled water. The solution was heated for 1-2 minutes in the microwave at low power until it reached a temperature of about 46-50° C. The solution was then filtered using filter paper. The to tree oil (NOW® Personal Care, Certified Organic; Bloomingdale, Ill.) was added to the heated solution, stirring vigorously. The solution was then filtered again using filter paper. Next, the immune stimulant extract was added to the filtered grape seed extract/tea tree oil solution and stirred. In a separate container, 100 ml of the antiseptic mouthwash were measured out, reserving the rest. The grapefruit seed extract was added and mixed well to form the second solution. The remaining antiseptic mouthwash (900 ml) was placed in a third container. Next, 3 ml of peppermint oil were added to the mouthwash, stirring vigorously until well-mixed, forming the third solution.

The second and third solutions were then combined as detailed above for Formulation A. The 100 ml mouthwash/grapefruit seed extract solution was added to the container containing the 900 ml of mouthwash. The combined solution was then placed in a large container. The first solution (water/grape seed solution) was then added to the combined mouthwash solution and stirred for about 1 minute. Finally, the 3% solution of hydrogen peroxide was added and the entire solution was lightly stirred to yield the inventive oral rinse solution.

The above procedure was repeated using 1.5 ml of peppermint oil and 1.5 ml of spearmint oil in place of the 3 ml of peppermint oil to yield a second composition. The pH of the resulting oral rinse composition was about 4.5-5.

TABLE 3

Formulation C

| Ingredient | Quantity |
| --- | --- |
| Antiseptic Mouthwash[A] | 1000 ml |
| Distilled water | 1000 ml |
| Hydrogen peroxide (3% solution) | 946.35 ml |

TABLE 3-continued

Formulation C

| Ingredient | Quantity |
| --- | --- |
| Grape Seed Extract powder | 1200 mg |
| Immune Stimulant Extract[B] | 6 ml |
| Grapefruit Seed Extract | 6 ml |
| Tea Tree Oil | 1 ml |
| Olive Leaf Extract | 15 ml |
| Essential Oil(s)[C] | 3 ml (total) |

[A]Same mouthwash from Formulation A.
[B]ECHINAMIDE ® Anti-V Formula, Natural Factors; Coquitlam, British Columbia, Canada.
[C]Peppermint oil, spearmint oil, clove oil, and combinations of the foregoing.

To prepare Formulation C, three separate solutions were made. For the first solution, the grape seed extract powder was stirred into 1000 ml of distilled water. The solution was heated for 1-2 minutes in the microwave at low power until it reached a temperature of about 46-50° C. The solution was then filtered using filter paper. The tea tree oil was added to the heated solution, stirring vigorously. The solution was then filtered again using filter paper. Next, the immune stimulant extract was added to the filtered aqueous solution and stirred. In a separate container, 100 ml of the antiseptic mouthwash were measured out, reserving the rest. The grapefruit seed extract was added and mixed well to form the second solution. The remaining antiseptic mouthwash (900 ml) was placed in a third container. Next, 3 ml of peppermint oil (flavoring agent) was added to the mouthwash, stirring vigorously until well-mixed, forming the third solution.

The second and third solutions were then combined as detailed above for Formulation A. The 100 ml mouthwash/grapefruit seed extract solution was added to the container containing the 900 ml of mouthwash/peppermint solution. The combined solution was then placed in a large container. The first solution (aqueous solution) was then added to the combined mouthwash solution and stirred for about 1 minute. Then the hydrogen peroxide was added and the entire solution was lightly stirred. Finally, the olive leaf extract (Herb Pharm® Olive Whole Leaf Extract; Williams, Oreg.) was added to the solution and stirred to yield the inventive oral rinse solution.

The above procedure was repeated using 1.5 ml of peppermint oil and 1.5 ml of spearmint oil in place of the 3 ml of peppermint oil to yield a further inventive composition.

The pH of the resulting oral rinse composition was about 4.5.

Example 2

Oral Rinse Formulation

This example describes how an oral rinse formulation according to the present invention will be prepared using the ingredients set forth in the table below.

TABLE 4

Formulation D

| Ingredient | Approximate Quantity |
| --- | --- |
| Distilled Water | 1400-1700 ml |
| Hydrogen Peroxide (3% solution) | 946.35 ml |
| Alcohol[1] | 216-269 ml |
| Sorbitol | 150-300 ml |
| Eucalyptol | 0.922 g |
| Menthol | 0.425 g |
| Methyl Salicylate | 0.600 g |
| Thymol | 0.639 g |
| Non-ionic surfactant[2] | 1.5-5.0 ml |
| Grape Seed Extract powder | 1.0-1.2 g |
| Immune Stimulant Extract | 5-6 ml |
| Citrus Seed Extract | 5-6 ml |
| Tea Tree Oil[x] | 1 ml |
| Olive Leaf Extract[x] | 15 ml |
| Benzoic Acid | 1.5 g |
| Additional Essential Oil(s) | 1-3 ml (total) |

[1]Ethanol, ethanol/1-propanol mixture.
[2]Poly(oxyethylene)-poly(oxypropylene) block copolymers, condensates of ethylene oxide with polymers of propylene oxide, and amphoteric agents such as quarternized imidazole derivatives
[x]Denotes an optional ingredient depending upon the formulation.

To prepare Formulation 1), three separate solutions will be made. In the first solution, the grape seed extract powder will be stirred into 1000 ml of distilled water. The solution will be heated for 1-2 minutes in the microwave at low power until it reaches a temperature of about 43-50° C., depending upon the amount of grape seed extract used. Higher temperatures will be used when more grape seed extract is used. The solution will then be filtered using filter paper. If tea tree oil is being used in the formulation, the tea tree oil will be added to the heated solution at this point, stirring vigorously. The solution will then be filtered again using filter paper. Next, the immune stimulant extract will be added to the filtered solution and stirred. If no tea tree oil is being used, the immune stimulant extract will be added after the heated solution is filtered.

In a separate container, 100 ml of the alcohol will be measured out, reserving the rest. The citrus seed extract will be added and mixed well to form the second solution. The remaining quantity of alcohol will be placed in a third container. The essential oils (eucalyptol, menthol, methyl salicylate, thymol, and peppermint, spearmint, and/or clove oil), benzoic acid, and non-ionic surfactant will then be added into the alcohol, stirring vigorously preferably until complete dissolution is achieved, forming the third solution.

Next, the second and third alcohol solutions will be combined. The 100 ml alcohol/grapefruit seed extract solution will be added to the container containing the alcohol and essential oils. The combined alcohol solution will then be placed in a large container. The first solution (aqueous solution) will then be added to the combined alcohol solution and stirred for about 1 minute. The 3% solution of hydrogen peroxide will be added and the entire solution will be lightly stirred, yielding the inventive composition. Alternatively, the olive leaf extract can be added to the solution after the hydrogen peroxide and stirred to form another of the inventive oral rinse solutions.

Additional distilled water is then added to q.s. the composition to a total volume of approximately 3000 ml.

Optional ingredients such as artificial sweeteners (sodium saccharin) and preservatives can then be added. Sodium benzoate will then be added as needed to adjust the pH of the solution to between about 4.5 and 6.0. Coloring will also be added as desired.

Example 3

Treatment of Patients Using Oral Rinse Composition

The oral rinse compositions prepared according to Formulations A-C in Example 1 above were used to treat 115 patients exhibiting various symptoms. Each patient was provided with a sample of the oral rinse composition with instructions to use the oral rinse twice a day for at least two weeks. Patients were instructed to swish and hold about 1 tablespoon of the solution in the mouth for about 30-60 seconds. During follow-up appointments, patients were asked to assess the oral rinses and provide feedback. Some of the patients were formally surveyed and asked to rate the results of the mouthwash in nine different categories. The rating was on a scale of 1 to 10, with 1 being the lowest or "ineffective" at alleviating symptoms, and 10 being the highest or "very effective" at alleviating symptoms. The profiles of the twenty-three respondents are provided in the table below.

| Patient Profiles | | | | |
|---|---|---|---|---|
| Patient | Age | Sex | Race | Condition(s)/Symptom(s) |
| 1 | 69 | M | Mid-East Indian | Periodontal maintenance, generalized gingival recession, mild to moderate hypersensitivity |
| 2 | 24 | M | Caucasian | Tooth Discoloration (VITA Shade A3.5) |
| 3 | 55 | F | African American | Food traps, pockets, inflamed gums |
| 4 | 39 | F | African American | Non-specific pain, food traps, several decaying and broken down teeth |
| 5 | 80 | M | African American | Stage I periodontal maintenance, gum pain |
| 6 | 57 | M | African American | Periodontitis, bleeding gums |
| 7 | 95 | F | African American | Periodontal maintenance, gum pain, pocket in lower right molar area |
| 8 | 56 | F | Caucasian | Periodontal maintenance, toothbrush abrasion, hypersensitivity |
| 9 | 52 | F | African American | Smoker, periodontal pockets, sensitive gums, mobile teeth lower molars |
| 10 | 49 | F | African American | Rotten/decayed teeth, required immediate full upper extractions, immediate upper denture and lower partial, chronic pain after extraction and insertion |
| 11 | 26 | F | African American | Non-restorable acute pupal pain and abscess, referred to oral surgeon, dry socket resulted |
| 12 | 57 | F | African American | Occlusal Trauma, TMJ dysfunction, hyper-occlusion, jaw pain, earache |
| 13 | 61 | F | African American | Stage I periodontal maintenance, aching gums, dry mouth |
| 14 | 54 | F | Caucasian | Inflamed and aphthous lesions (mouth sores) |
| 15 | 20 | F | African American | Inflamed and irritated gums due to orthodontic appliances (braces) |
| 16 | 60 | F | Caucasian | Occlusal Trauma, TMJ dysfunction, missing and non-restored teeth |
| 17 | 51 | F | African American | Smoker, Stage II periodontal disease, painful lateral periodontal abscess at partial abutting tooth, could not use partial |
| 18 | 44 | F | African American | Large Class II distal cavity in tooth #31, packed food against 3rd molar with gingival damage, referred to oral surgeon |
| 19 | 54 | F | African American | Class II distal cavity in molar #19, pain and soreness, cracked tooth |
| 20 | 53 | M | African American | Throbbing pain in lower molar under crown (bridge), non-restorable abscessed tooth, extraction and subsequent dry socket |
| 21 | 52 | F | African American | Occlusal Trauma, cracked tooth #13 (eventual root canal), ulcer (canker sore) at upper right palatal area |
| 22 | 72 | F | African American | Surgical extraction post-operative care |
| 23 | 68 | M | Caucasian | Halitosis |
| 24 | 62 | M | Caucasian | Diabetic patient, Chronic non-compliant, diabetic-induced periodontitis, dry mouth, abscess |

The results of the survey for each patient who provided a rating for one or more categories are provided below.

| | Patient | Usage | Pain | Bleeding | Sensitivity | Odor | Inflammation | Discoloration | Calculus Formation | Clean Feel | Healing |
|---|---|---|---|---|---|---|---|---|---|---|---|
| Formulation A | 1 | 2 wks. | 8 | 10 | 5 | 10 | 8 | 5 | 8 | 10 | 8 |
| | 2 | 3 mos. | — | — | — | 10 | 10 | 9 | 10 | 10 | — |
| | 3 | 3 wks. | 10 | 10 | 10 | 8 | 10 | — | — | 9 | 8 |
| | 4 | 5 wks. | — | 8 | 7 | 8 | 7 | — | — | 8 | 7 |
| | 5 | 18 days | 10 | 10 | 10 | 10 | 10 | — | — | 10 | 10 |
| | 6 | 18 days | — | 10 | — | 10 | 7 | 6 | 6 | 7 | 6 |
| | 7 | 1 mo. | 9 | 9 | 9 | 10 | 9 | 9 | 9 | 7 | 6 |
| Formulation B | 8 | 12 days | 8 | 8 | 8 | — | 7 | 6 | 6 | 7 | 6 |
| | 9 | 3 wks. | 10 | 1 | 1 | 10 | 1 | 10 | — | 10 | 1 |
| | 10 | 1 mo. | 10 | 10 | 10 | — | 10 | — | — | — | 10 |
| | 13 | — | 6 | 8 | 6 | 10 | 6 | 8 | — | 10 | 6 |
| | 14 | 8 mos. | 9 | 9 | 9 | 10 | 9 | 7 | 9 | 7 | 10 |

-continued

Survey Results

| | Patient | Usage | Pain | Bleeding | Sensitivity | Odor | Inflammation | Discoloration | Calculus Formation | Clean Feel | Healing |
|---|---|---|---|---|---|---|---|---|---|---|---|
| Formulation C | 16 | 7 days | 10 | — | 10 | 10 | 10 | — | — | — | 10 |
| | 17 | 3 wks. | 10 | 9 | 10 | 8 | 10 | 10 | — | — | — |
| | 18 | — | 10 | — | — | 9 | — | — | — | — | 9 |
| | 19 | 2 wks. | 10 | — | — | 10 | — | — | — | 10 | — |
| | 20 | — | 7 | 10 | 5 | 8 | 10 | 5 | 7 | 8 | 5 |
| | 21 | 7 days | 8 | — | 8 | 8 | 8.5 | 8 | — | — | 10 |
| | 22 | daily | 9 | — | — | 10 | — | — | — | 10 | — |
| | 23 | 3 wks. | — | — | — | 10 | — | — | — | 10 | — |
| | 24 | 2 mos. | — | 8 | — | 8 | 10 | — | — | 10 | 10 |

Discussion

Patient 11 was an emergency walk-in patient with non-restorable acute pupal pain and abscess, as noted in the Patient Profile table above. She was referred to an oral surgeon for an extraction. Post-extraction she developed a dry socket. Traditionally, to treat dry socket a medicated dressing containing analgesics and antiseptics is lightly packed into the open socket. The dressing is changed daily. Instead of returning to the oral surgeon for conventional treatment, Patient 11 was treated with oral rinse Formulation B. Patient 11 reported that after 0.3-5 days the dry socket had resolved itself.

Patient 12 presented with progressively worsening jaw pain over several months, eventually radiating into an earache. Patient 12 was treated with oral rinse Formulation B for a period of two and half weeks. During the follow-up appointment, Patient 12 reported that he no longer had jaw pain or an earache.

Patient 13 exhibited Stage I periodontal disease and had been previously prescribed a prescription oral rinse, PERIDEX™. Patient 13 was treated with oral rinse Formulation B. At a follow-up appointment, Patient 13 reported that Formulation B was preferable to the prescription oral rinse because it left her mouth feeling refreshed and had less of a burning sensation as compared to the prescription rinse.

Patient 18 presented as a walk-in emergency patient with extreme pain due to a large cavity as noted in the Patient Profile table above. She reported that over the weekend she had already tried over-the-counter toothache medicine and pain relievers without relief. Patient 18 was referred to an oral surgeon and also instructed to use oral rinse Formulation C in the interim. At a follow-up, the patient reported that Formulation C immediately relieved the pain until her next appointment to have the cavity treated. She also reported that it seemed to help in healing her gums. She used the oral rinse until completion of her treatment by the surgeon.

Patient 20 was another emergency patient who presented with a non-restorable abscessed tooth. The tooth was extracted at the next appointment and the patient subsequently developed a dry socket. Patient 20 was unable to take time off from work to have the dry socket treated. The patient was instructed to use oral rinse Formulation C for approximately one week. The patient reported that despite lack of traditional treatment, the dry socket had resolved itself.

I claim:

1. An aqueous composition comprising:
an essential oil selected from the group consisting of eucalyptol, menthol, methyl salicylate, thymol, tea tree oil, peppermint, spearmint, clove, and mixtures thereof;
from about 15% to about 65% v/v hydrogen peroxide;
less than about 20% v/v alcohol;
from about 0.001% to about 0.10% w/v grape seed extract;
citrus seed extract, said citrus seed extract consisting of grapefruit seed extract; and
immune stimulant, said immune stimulant being selected from the group consisting of Echinacea, Goldenseal, Hawthorne Berry, Myrrh, Rosehips, Lomatium dissectum, Astragalus root, Licorice root, and mixtures thereof.

2. The composition of claim 1, wherein said composition comprises:
from about 0.005% to about 1.0% v/v of said citrus seed extract; and
from about 0.005% to about 1.0% v/v of said immune stimulant.

3. The composition of claim 1, said composition comprising less than about 7.5% v/v alcohol.

4. The composition of claim 1, said composition having a pH of from about 4.0 to about 6.5.

5. The composition of claim 1, wherein said alcohol is selected from the group consisting of ethanol, 1-propanol, 2-propanol, 1-butanol, 2-butanol, 2-methyl-2-propanol, propylene glycol, and mixtures thereof.

6. The composition of claim 1, wherein said essential oil comprises a mixture of:
from about 0.001% to about 0.065% v/v tea tree oil;
from about 0.005% to about 0.50% v/v of a first essential oil selected from the group consisting of peppermint oil, spearmint oil, clove oil, and mixtures of the foregoing; and
a second essential oil selected from the group consisting of eucalyptol, menthol, methyl salicylate, thymol, and mixtures thereof.

7. The composition of claim 6, said composition further comprising from about 0.01% to about 2.0% v/v olive leaf extract.

8. The composition of claim 1, further comprising a sugar alcohol selected from the group consisting of xylitol, sorbitol, mannitol, maltitol, lactitol, isomalt, hydrogenated starch hydrosylate, erthyritol, and mixtures thereof.

9. An aqueous solution consisting essentially of:
water;
hydrogen peroxide;
less than about 20% v/v alcohol selected from the group consisting of ethanol, 1-propanol, 2-propanol, 1-butanol, 2-butanol, 2-methyl-2-propanol, propylene glycol, and mixtures thereof;
grape seed extract;
citrus seed extract consisting of grapefruit seed extract;
immune stimulant selected from the group consisting of Echinacea, Goldenseal, Hawthorne Berry, Myrrh, Rosehips, Lomatium dissectum, Astragalus root, Licorice root, and mixtures thereof;

sugar alcohol selected from the group consisting of xylitol, sorbitol, mannitol, maltitol, lactitol, isomalt, hydrogenated starch hydrosylate, erthyritol, and mixtures thereof; and from about 0.01% to about 0.50% total essential oils, based upon the total volume of the aqueous solution taken as 100% by volume, said essential oils being selected from the group consisting of eucalyptol, menthol, methyl salicylate, thymol, tea tree oil, peppermint, spearmint, clove, and mixtures thereof.

* * * * *